US006858776B1

(12) United States Patent
Podila et al.

(10) Patent No.: US 6,858,776 B1
(45) Date of Patent: Feb. 22, 2005

(54) PLANTS HAVING MODIFIED REPRODUCTIVE CAPACITY

(75) Inventors: Gopi Krishna Podila, Houghton, MI (US); Jun-Jun Liu, Houghton, MI (US); David F. Karnosky, Chassell, MI (US)

(73) Assignees: Carter Holt Harvey Limited, Manakau City (NZ); Rubicon IP Limited, Auckland (NZ); Michigan Technological University, Houghton, MI (US)

( * ) Notice: Subject to any disclaimer, the term of this patent is extended or adjusted under 35 U.S.C. 154(b) by 0 days.

(21) Appl. No.: 09/936,869

(22) PCT Filed: Mar. 17, 2000

(86) PCT No.: PCT/NZ00/00031

§ 371 (c)(1),
(2), (4) Date: Mar. 29, 2002

(87) PCT Pub. No.: WO00/55172

PCT Pub. Date: Sep. 21, 2000

(30) Foreign Application Priority Data

Mar. 17, 1999 (NZ) .............................................. 334715

(51) Int. Cl.[7] ........................ C12N 15/82; C12N 15/29; C12N 15/56; C12N 5/04; A01H 5/00
(52) U.S. Cl. ...................... 800/287; 800/278; 800/286; 800/288; 800/290; 800/319; 800/323; 435/199; 435/419; 536/23.6; 536/24.1; 536/24.5
(58) Field of Search ................................ 800/278, 286, 800/287, 288, 290, 319, 323; 435/199, 419; 536/23.6, 24.1, 24.5

(56) References Cited

U.S. PATENT DOCUMENTS 6,395,892 B1 * 5/2002 Strauss et al. .............. 536/24.1
6,444,877 B1 * 9/2002 Rottmann .................... 800/285

FOREIGN PATENT DOCUMENTS

| EP | 967278 | 12/1999 | ........... C12N/15/29 |
| WO | WO 98/13503 | * 4/1998 | |
| WO | WO 98/44138 | 10/1998 | .......... C12M/15/82 |

OTHER PUBLICATIONS

Birren et al. Accession No. AC119185 (Mar. 2003).*
Roberts et al. Sexual Plant Reproduction 8(5): 299–307 (1995).*
Mouradov et al. Developmental Genetics 25: 245–252 (1999).*
Turgut et al. Plant Molecular Biology 24(1): 97–104 (1994).*
Kim et al. Plant Molecular Biology 24(1): 105–117 (1994).*
Garland Publishing, Inc.: New York. pp. 551–612 In: Molecular Biology of the Cell. (1989).*
Tandre et al. Accession No. PADAL2 (Feb. 1995).*
Faktor, O., "Functional dissection of a bean chalcone synthase gene promoter in transgenic tobacco plants reveals sequence motifs essential for floral expression" (1996) Plant Molecular Biology 32:849–859.
Tandre, K. et al., "Conservation of gene structure and activity in the regulation of reproductive organ development of conifers and angiosperms" (Sep. 1998) The Plant Journal 15(5):615–623.
Liu, J. et al., Pinus radiata MADS box protein mRNA, complete cds, GenBank Accession AF023615 (Jan. 1999).
Rutledge, R. et al., Characterization of a AGAMOUS homologue from the conifer Black Spruce (*Picea mariana*) that produces floral homeotic conversions when expressed in Arabidopsis (Sep. 1998) The Plant Journal 15(5):625–634.
Rutledge, R. et al., *Picea mariana* AGAMOUS–like MADS–box transcriptional factor SAG1a mRNA, complete cds, GenBank Accession U69482, (Jan. 2000) (references Rutledge 1998).
Rutledge, R. et al., *Picea mariana* AGAMOUS–like MADS–box transcription factor SMADS42B mRNA, complete cds, GenBank Accession U46582, (Dec. 1998).
Taylor, C. et al., "RNS2: A senescence–associated RNase of Arabidopsis that diverged from S–RNases before speciation" (1993) Proceedings of the National Academy of Science, USA 90(11):5118–5122.

* cited by examiner

Primary Examiner—David T. Fox
(74) Attorney, Agent, or Firm—Greenlee Winner and Sullivan PC

(57) ABSTRACT

This invention relates to plants having modified reproductive capacity. In particular, it relates to a plant reproductive tissue specific promoter, the PrAG1 promoter isolated from *Pinus radiata*, and its use in promoting transcription/expression of associated sequences in plant reproductive tissue, including for the purpose of producing plants which have diminished reproductive capacity or which are sterile.

30 Claims, 7 Drawing Sheets

```
TGT GTA CAA ATC ATG GGT CGT GGG AAG ATT GAG ATA AAG AGG ATT GAA AAT ACT   54
                M   G   R   G   K   I   E   I   K   R   I   E   N   T

ACG AAC CGA CAG GTC ACT TTC TGC AAG CGC CGA AAT GGT TTA TTA AAG AAG GCG  108
 T   N   R   Q   V   T   F   C   K   R   R   N   G   L   L   K   K   A

TAT GAA TTA TCA GTT CTT TGT GAT GCA GAA GTG GCC CTC ATC GTC TTC TCC AGC  162
 Y   E   L   S   V   L   C   D   A   E   V   A   L   I   V   F   S   S

AGA GGG AGA CTT TAT GAA TTT GCC AAC CAC AGC GTG AAG AGG ACG ATT GAG AGG  216
 R   G   R   L   Y   E   F   A   N   H   S   V   K   R   T   I   E   R

TAC AAG AAG ACT TGC GTT GAC AAC AAC CAC GGA GGG GCG ATA TCA GAG TCC AAT  270
 Y   K   K   T   C   V   D   N   N   H   G   G   A   I   S   E   S   N

TCT CAG TAT TGG CAA CAG GAG GCT GGT AAA CTC AGA CAA CAG ATT GAC ATT TTG  324
 S   Q   Y   W   Q   Q   E   A   G   K   L   R   Q   Q   I   D   I   L

CAA AAT GCA AAT AGG CAT TTG ATG GGT GAC GGG CTT ACA GCT TTG AAC ATT AAG  378
 Q   N   A   N   R   H   L   M   G   D   G   L   T   A   L   N   I   K

GAA CTC AAG CAA CTT GAG GTT CGA CTT GAA AAA GGA ATC AGC CGA GTG CGA TCC  432
 E   L   K   Q   L   E   V   R   L   E   K   G   I   S   R   V   R   S

AAA AAG AAC GAG ATG TTG CTT GAA GAG ATC GAC ATC ATG CAG AGA AGG GAA CAC  486
 K   K   N   E   M   L   L   E   E   I   D   I   M   Q   R   R   E   H

ATA CTT ATC CAG GAG AAT GAG ATT CTT CGC AGC AAG ATA GCC GAG TGT CAG AAT  540
 I   L   I   Q   E   N   E   I   L   R   S   K   I   A   E   C   Q   N

AGC CAC AAC ACG AAC ATG TTA TCA GCT CCG GAA TAT GAT GCA CTG CCC GCA TTC  594
 S   H   N   T   N   M   L   S   A   P   E   Y   D   A   L   P   A   F

GAC TCT CGA AAT TTC CTA CAT GCA AAT CTA ATC GAT GCG GCC CAT CAC TAT GCA  648
 D   S   R   N   F   L   H   A   N   L   I   D   A   A   H   H   Y   A

CAT CAG GAA CAA ACA ACG CTT CAG CTT GGC TGA ACG TTG AAG CGG TGG ACG CTT  702
 H   Q   E   Q   T   T   L   Q   L   G   *

AAA ACT CAA TCA AGG CAC CCG AAA AAT ATG CTA GTA ACC TTG AAT GAG ATT CAG  756

AGT CGA AAT ATT GCG AGG CAA GAG CAC AAT GGA AGA GAT AGC TCC TAG TAT GAA  810

TAT GGA TTT ATG ATA TTA ACA TAT GGT TTG TCA GCT TTA AAT ATA GCT GTT TGA  864

AAC AAA GAA TAC AAC ATA TTA GCT AGT ATT TTT TTG GCG CAT GTT ATC TTT CTG  918

TTG                                                                      921
```

FIGURE 1

```
AAACTCGACAGCAAATATGATTTAGATTATGACCTAGAAATAAGCATAGCATTAAAGCAT   60
ATACATAACAAGCGGTGATATACTCTGACTGCCACTGTACTTGAGGAAAGGTAGTGGACT  120
CTGCTCAGGTACATTAGTTTGGTAAGGTTGGCTTGGCTTCTGGGTAATATGAGAAGTAAA  180
GAAGTAAAAGGTATTTGACTCTAGTCAAGTACATTGGATTGCCTTTGTCGGGGCTTGGAT  240
GGCTTGGGTTCGTGTGAGAAGCCAACAATTTATAAGAAATATATAAAATAAAAAATAAAA  300
AAATTTAAGTGTTGGAAGTGAAAACGGTGGGGCAGAAATATACACAGAAGAGTACTTTAA  360
CAATGCGCAACCAAGGCAGATTCACAACTTGATTTCTGGACCTCGAATACGAGATAATGG  420
TGGTAAGAAATAAAGGAAGAGTGGAGTGCATTTGAAAATGAATGGAGAGCGCACAAAATG  480
GAGGACGAATAAATGAAATATAATGCAAGAGTGCATTTCCCTATTATTTCCAGAAATGTA  540
TATGTGGGGTCGGCATTCACATGGGCGTCGCATTCAGGGGGTGTCATAGCGGTCCTTTGA  600
TTGCAGTGTGGGAGTTGCAACATGTACCAACAAATCCATTCATCCCAAAACCTAAATTTA  660
TCCTCTCCATTACTATTACCTACACCTATACCTAGTAAATATGTCCTGCCTTGTAACTCC  720
TCCACTGCCTGCACACGTCTTAGTCAATCCATCTGCCTTCAAATAGGCATTATTTTGTTC  780
TTTCCCCTCCGACTGAAAGGCTATCGACCGACCGACCGCTCATCTTCTTCTTCTGCGCAA  840
TTTTTTCTGCTGGATCATCATCATTACCATCATCGCCATCCCCACCATCATCATCATGAT  900
GGTATCTCTATCTCTCCCTGGCAATCGATTGTAGAGGAAAGGAAGAGGGAAGGGGCATAT  960
GTATTGATCAACCTACCCGAAAAAACAATCTGATCAGCCCTGCTCAATCTTGCTTATAAA 1020
TCTCTTATCCACTGTTCAATCATTCAGGTTTCTTCCCACTTTCAAGCAAAGGCGCCCGGA 1080
TTGGCCGTGTTCTTAGATTTTCAGGTACTTAAATGGACAATATTCCCCACCTGAAGCCGT 1140
TCTGAAAAGATTTGTTTGTAGAAACAAACGATTGTAATATTTGCTTAAGTTGAGCTTAA  1200
GGGGTTTGGTACCTAACTTGCCTTGTGGTTATTTGTTTCTCAGAACTCGGGCTGCGTCCA 1260
ACTGTAGGAACGAACCAGCACAAGGGGTTGCAGCTTTTGCTGTTGCTGTTGCGCCCATTG 1320
CTTTTGGACTGGTATTAGTAGTTGCAGCTTTGTTTTGCATACGCTGTGAGGATCTGTGCG 1380
CGGAAATTTTGTGTACAAATC                                        1401
```

PLANTS HAVING MODIFIED REPRODUCTIVE CAPACITY

This application was filed under 35 U.S.C. 371, based on PCT/NZ00/00031, which application was filed Mar. 17, 2000 and claims priority from New Zealand Application No. 334715, filed March 17; 1999.

This invention relates to plants having modified reproductive capacity. In particular, it relates to a plant reproductive tissue specific promoter and its use in promoting transcription/expression of associated genes in plant reproductive tissue, including for the purpose of producing plants which have diminished reproductive capacity or which are sterile.

INTRODUCTION

It is desirable that the genetic basis of reproduction/flower development in plants be determined. Identification of genes involved in plant reproduction and/or flower development together with the regulatory elements which control their expression in reproductive tissue allows for modulation of the reproductive capacity of plants and specifically enables the production of reproductively null (sterile) plants.

Identification of the regulatory elements involved further allows for the expression in reproductive tissue of genes which are heterologous to the plant where that is desirable.

The applicants have now identified and isolated such a reproductive tissue specific promoter which endogenously regulates expression of a peptide involved in the reproductive cycle of *Pinus radiata*. It is broadly towards this promoter, to its homologs in other plants and to its use in effecting expression of associated genes within the reproductive tissue of plants that the present invention is directed.

SUMMARY OP THE INVENTION

In a first aspect, the present invention provides a polynucleotide which has a nucleotide sequence of from nucleotides 1 to 1320 of FIG. 2 and which has the ability, when operatively associated with a nucleotide sequence encoding a peptide, to promote transcription of that nucleotide sequence, or a polynucleotide which is a functionally equivalent variant thereof.

In a second aspect, the invention provides a plant reproductive tissue promoter which has a nucleotide sequence of from nucleotides 1 to 1320 of FIG. 2, or a functionally equivalent variant thereof.

In a further aspect, the invention provides a DNA construct which comprises:
 (a) a polynucleotide having activity as a transcriptional promoter as described above;
 (b) an open reading frame polynucleotide coding for a peptide; and
 (c) a termination sequence.

In yet a further aspect, the invention provides a DNA construct which comprises:
 (a) a promoter sequence as defined above;
 (b) an open reading frame polynucleotide coding for a peptide; and
 (c) a termination sequence.

In each construct the open reading frame can be in a sense orientation, or an anti-sense orientation.

In one embodiment, the open reading frame polynucleotide encodes a peptide having the sequence of FIG. 1.

In other embodiments, the open reading frame polynucleotide encodes a peptide which, when expressed in reproductive tissue of a plant, causes said plant's reproductive organs to abort, to redefine themselves as vegetative, or to stop development.

In still another embodiment, the open reading frame polynucleotide encodes a peptide which, when expressed in the reproductive tissue of a plant, causes cell death.

In yet another embodiment, the open reading frame polynucleotide encodes a peptide, which when expressed in reproductive tissue of a flowering plant, causes an alteration in the timing of flowering of said plant.

In a preferred form, the construct further includes:
 (d) a selection marker sequence.

In a further aspect, the invention provides a transgenic plant cell which includes a construct as described above.

By "transgenic" as used herein, the applicants mean containing non-endogenous genetic material.

In another aspect, the invention provides a transgenic plant which includes a construct as described above.

In still another aspect, the invention provides a transgenic plant which contains a polynucleotide having activity as a transcriptional promoter as described above or a reproductive tissue promoter as described above, which plant has a reduced reproductive capacity.

It is particularly preferred that the plant be sterile.

Conveniently, in said plant said polynucleotide or promoter is operatively associated with a nucleotide sequence encoding a RNAse.

The plant can be a coniferous plant, such as a coniferous plant of the *Pinus* genus, or a tree such as a member of the *Eucalyptus* genus.

It is particularly preferred that the transgenic plant be a member of a species selected from *Pinus radiata, Pinus taeda, Pinus elliotti, Pinus cause, Pinus palustrus, Pinus echinata, Pinus ponderosa, Pinus jeffrey, Pinus resinosa, Pinus rigida, Pinus banksiana, Pinus serotina, Pinus strobus, Pinus monticola, Pinus lambertiana, Pinus virginiana, Pinus contorta, Pinus cariboea, Pinus pinaster, Pinus brutia, Pinus eldarica, Pinus coulteri, Pinus nigra, Pinus sylvestris, Pinus tecunumannii, Pinus keysia, Pinus oocarpa* and *Pinus maxinumoii*.

DESCRIPTION OF THE DRAWINGS

While the invention is broadly as defined above, it will be appreciated by those persons skilled in the art that it is not limited thereto and that it further includes embodiments of which the following description provides examples. In addition, the invention will be better understood through reference to the accompanying drawings in which:

FIG. 1 shows the amino acid sequence (SEQ ID NO:4) of the reproductive peptide PrAG1, together with the nucleotide sequence coding therefor (SEQ ID NO:3):

FIG. 2 shows the sequence of the PrAG1 promoter, which is the focus of the present invention, isolated from *Pinus radiata* (SEQ ID NO:2):

DESCRIPTION OF THE INVENTION

Figure 3:
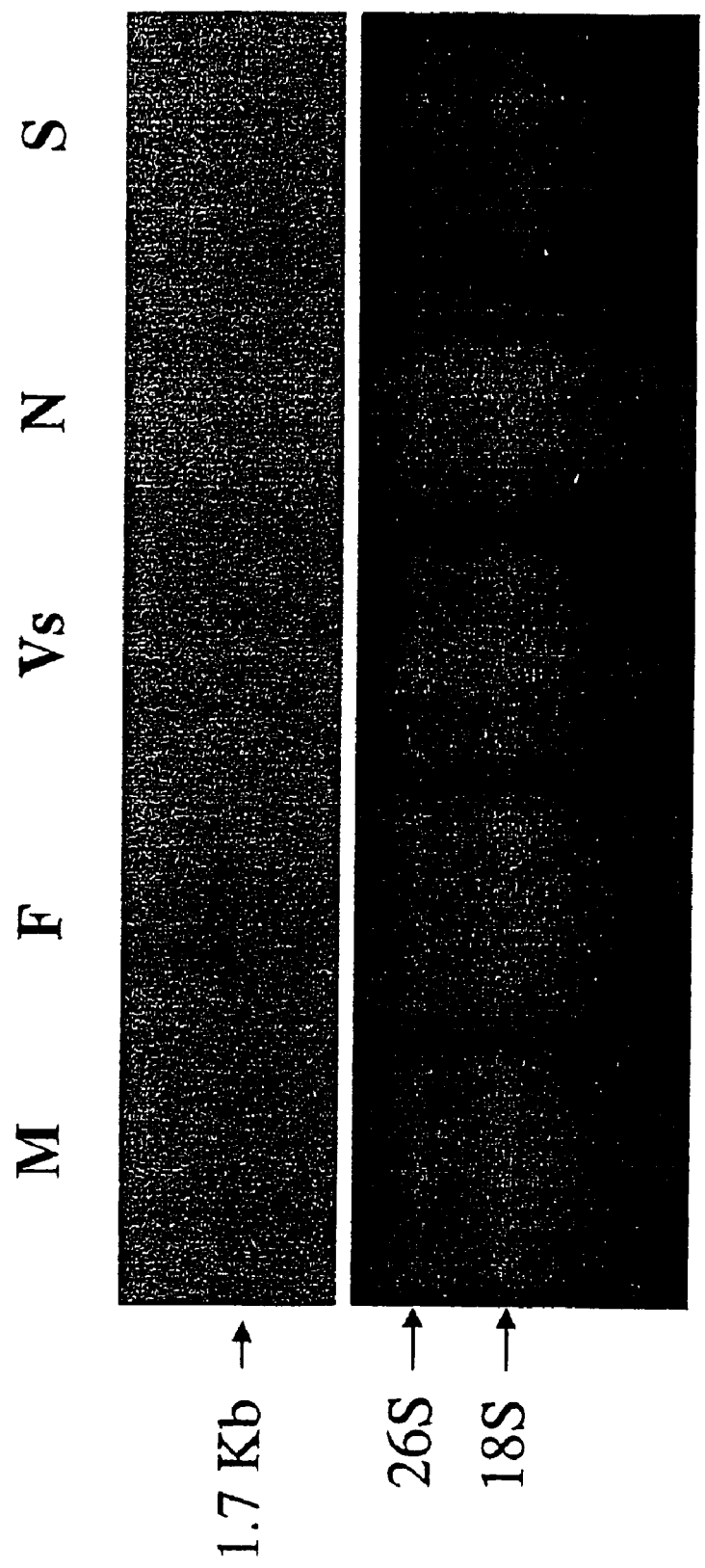
FIG. 3 is an RNA gel blot analysis of PrAG1 mRNA accumulation in *Pinus radiata* organs. Twenty µg of total RNA from various organs was electrophoresed, blotted onto nylon membranes, and hybridized with 3'-terminal fragment of PrAG1 cDNA. Total RNA was isolated from immature male cone (M), immature female cone (F), vegetative shoot (V)s, needle (N) and stem (S). The 26S and 18S rRNA was used as control (bottom)

As broadly outlined above, the applicants have identified a plant promoter which is involved in plant reproduction. The promoter, which was isolated from *Pinus radiata* is called herein the "PrAG1 promoter".

The nucleotide sequence of the PrAG1 promoter is given in FIG. 2 from nucleotides 1 to 1320. It will however be appreciated that the invention is not restricted only to the polynucleotide having that specific nucleotide sequence. Instead, the invention also extends to functionally equivalent variants of that polynucleotide.

The phrase "functionally equivalent variants" recognises that it is possible to vary nucleotide sequence while retaining substantially equivalent functionality. Variants can have a greater or lesser degree of homology as between the variant nucleotide sequence and the original.

Polynucleotide sequences may be aligned, and percentage of identical nucleotides in a specified region may be determined against another sequence, using computer algorithms that are publicly available. Two exemplary algorithms for aligning and identifying the similarity of polynucleotide sequences are the BLASTN and FASTA algorithms. The BLASTN software are available on the NCBI anonymous FTP server (ftp://ncbi.nlm.nih.gov) under /blast/executables/. The BLASTN algorithm version 2.0.4 [Feb. 24, 1998], set to the default parameters described in the documentation of variants according to the present invention. The use of the BLAST family of algorithms, including BLASTN, is described at NCBI's website at URL http://www.ncbi.nlm.nih.gov/BLAST/newblast.html. The computer algorithm FASTA is available on the Internet at the ftp site ftp://ftp.virginia.edu/pub/fasta/. Version 2.0 u4, February 1996, set to the default parameters described in the documentation and distributed with the algorithm, is also preferred for use in the determination of variants according to the present invention. The use of the FASTA algorithm is described in W. R. Pearson and D. J. Lipman, "Improved Tools for Biological Sequence Analysis", *Proc. Natl. Acad. Sci. USA* 85:2444–2448 (1988).

The following running parameters are preferred for determination of alignments and similarities using BLASTN that contribute to E values (as discussed below) and percentage identity Unix running command: blastall -p blastn -d embldb -e 10 -G 1 -E 1 -r 2 -v 50 -b 50 -I queryseq -o results; and parameter default values:
-p Program Name [String]
-d Database [String]
-e Expectation value (E) [Real]
-G Cost to open a gap (zero invokes default behaviour) [Integer]
-E Cost to extend a cap (zero invokes default behaviour) [Integer]
-r Reward for a nucleotide match (blastn only) [Integer]
-v Number of one-line descriptions (V) [Integer]
-b Number of alignments to show (B) [Integer]
-i Query File [File In]
-o BLAST report Output File [File Out] Optional The "hits" to one or more database sequences by a queried sequence produced by BLASTN, FASTA, or a similar algorithm, align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms also produce "Expect" or E values for alignments. The E value indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. By this criterion, the aligned and matched portions of the sequences then have a 90% probability of being the same. For sequences having an E value of 0.01 or less over aligned and matched portions, the probability of finding a match by chance in the EMBL database is 1% or less using the BLASTN or FASTA algorithm.

It is also recognised that as the function of the polynucleotide is as a transcriptional promoter there are regions of the polynucleotide which are more critical to, and characteristic of, this function than others. An example are the TATA boxes at positions 280 to 286, 282 to 288 and 1015 to 1021 from the 5' end of the sequence. Therefore, polynucleotides which include these regions of the polynucleotide of FIG. 2 and have equivalent transcriptional functionality are contemplated variants, even where there is a lesser degree of homology elsewhere in the sequence.

According to one embodiment, "variant" polynucleotides, with reference to the polynucleotide of the present invention, preferably comprise sequences having the same number or fewer nucleic acids than the polynucleotide of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the parameters discussed above.

Variant polynucleotide sequences will also generally hybridize to the recited polynucleotide sequence under stringent conditions. As used herein, "stringent conditions" refers to prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

It is of course expressly contemplated that homologs to the PrAG1 promoter exist in other plants, particularly other coniferous plants, including other members of the *Pinus* genus. Such homologs are also "functionally equivalent variants" of PrAG1 promoter as the phrase is used herein.

DNA sequences from plants other than *Pinus radiata* which are homologs of the PrAG1 promoter may be isolated by high throughput sequencing of cDNA libraries prepared from such plants. Alternatively, oligonucleotide probes based on the sequence for the PrAG1 promoter provided in FIG. 2 can be synthesized and used to identify positive clones in either cDNA or genomic DNA libraries from other plants by means of hybridization or PCR techniques. Probes should be at least about 10, preferably at least about 15 and most preferably at least about 20 nucleotides in length. Hybridization and PCR techniques suitable for use with such ligonucleotide probes are well known in the art. Positive clones may be analyzed by restriction enzyme digestion, DNA sequencing or the like.

The polynucleotides of the present invention may be generated by synthetic means using techniques well known in the art. Equipment for automated synthesis of oligonucleotides is commercially available from suppliers such as Perkin Elmer/Applied Biosystems Division (Foster City, Calif.) and may be operated according to the manufacturer's instructions.

The PrAG1 promoter of the invention is plant reproductive-tissue-specific. The primary importance of identification of the polynucleotide of the invention is therefore that it enables the reproductive capacity of plants to be modulated. This modulation will generally involve a reduction in the reproductive capacity of the plant.

Any conventional technique for effecting this can be employed. Examples include co-suppression or anti-sense strategies, a dominant negative approach, or techniques which involve expressing enzymes (such as RNAses) to digest, or otherwise be lethal to, RNA post-transcription of a target gene.

Co-suppression can be effected in a manner similar to that discussed, for example, by Napoli et al (Plant Cell 2:279–290, 1990) and de Carvalho Niebel et al (Plant Cell 7:347–258, 1995). In some cases, it can involve overexpression of the gene of interest through use of multiple constructs of the PrAG1 promoter and gene to be suppressed.

Anti-sense strategies involve using the PrAG1 promoter to effect expression or transcription of DNA with the expression/transcription product being capable of interfering with translation of mRNA transcribed from the gene to be suppressed. This will normally be through the expression/transcription product hybridising to and forming a duplex with the target mRNA.

The expression/transcription product can be a relatively small molecule and still be capable of disrupting mRNA translation. However, the same result is achieved by expressing the target gene in an anti-sense orientation such that the RNA produced by transcription of the anti-sense oriented gene is complementary to all or part of the endogenous target mRNA.

Such anti-sense strategies are described generally by Robinson-Benion et al., (1995), Anti-sense techniques, *Methods in Enzymol.* 254(23):363–375 and Kawasaki et al., (1996), *Artific. Organs* 20 (8): 836–848.

Dominant negative approaches involve using the PrAG1 promoter to effect the expression of a modified DNA binding/activating protein which includes a DNA binding domain but not a activator domain. The result is that the protein binds to DNA as intended but fails to activate, while at the same time blocking the binding of the DNA binding/activating peptides which normally bind to the same site.

It is however presently preferred that the reproductive capacity of the plant be reduced or eliminated through the use of the PrAG1 promoter to drive transcription and expression of a nucleotide sequence which encodes an RNAse within the plant reproductive tissue. Such an approach, in which the PrAG1 promoter is coupled to the RNAse, RNS2, is exemplified herein.

To give effect to the above strategies, the invention also provides DNA constructs. The constructs include the PrAG1 promoter sequence, the DNA intended to be transcribed/expressed (such as the PrAG1 gene in sense or in anti-sense orientation or a polynucleotide encoding an RNAse) and a termination sequence, operably linked to the DNA sequence to be transcribed. The promoter sequence is generally positioned at the 5' end of the DNA sequence to be transcribed, and is employed to initiate transcription of the DNA sequence.

The DNA with which the PrAG1 promoter is operatively associated can encode any peptide it is desirable to express in plant reproductive tissue. As indicated above, this includes the peptide encoded by PrAG1, but can also be another peptide. That other peptide can be a peptide which, when produced, causes the reproductive organs of the plant to abort, redefine themselves as vegetative or stop development. The peptide encoded can, for example, also be a peptide causing cell death. Illustrative peptides/genes are Diphtheria Toxin A (DTA), Barnase (from *Bacillus amyloliquefaciens*), apoptosis genes, glucanase, and RNAses, with the selection of each being a matter of choice for the art skilled worker.

Alternatively, the peptide which is to be expressed under the control of the PrAG1 promoter can be one which, when produced, alters the timing of flowering (ie. either delays or accelerates flowering, such as the ELF-3 and CONSTANS flowering time genes).

The peptide to be expressed can be ligated to the promoter in a sense or antisense orientation, dependant upon the desired effect.

The termination sequence, which is located 3' to the DNA sequence to be transcribed, may come from the same gene as the PrAG1 promoter or may be from a different gene. Many termination sequences known in the art may be usefully employed in the present invention, such as the 3' end of the *Agrobacterium tumefaciens* nopaline synthase gene. However, preferred termination sequences are those from the original gene or from the target species to be transformed.

The DNA constructs of the present invention may also contain a selection marker that is effective in plant cells, to allow for the detection of transformed cells containing the construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al., in *Methods for Plant Molecular Biology*, A Weissbach and H Weissbach eds, Academic Press Inc., San Diego, Calif. (1988)). Other examples of markers include visible selection markers such as Green Fluorescent Protein (GFP) and herbicide resistance genes. Alternatively, the presence of the desired construct in transformed cells can be determined without reference to marker genes, by means of other techniques well known in the art, such as Southern and Western blots.

Techniques for operatively linking the components of the DNA constructs are well known in the art and include the use of synthetic linkers containing one or more restriction endonuclease sites as described, for example, by Maniatis et al., (*Molecular Cloning: A Laboratory Manual*, Cold Spring Harbour Laboratories, Cold Spring Harbour, N.Y., 1989). The DNA construct may be linked to a vector having at least one replication system, for example, *E. coli*, whereby after each manipulation, the resulting construct can be cloned and sequenced and the correctness of the manipulation determined.

The DNA constructs of the present invention may be used to transform a variety of plants. In one embodiment, these will be plants of the *Pinus* genus. In a preferred embodiment, the DNA constructs are employed to transform *Pinus radiata, Pinus taeda, Pinus elliotti, Pinus clausa, Pinus palustrus, Pinus echinata, Pinus ponderosa, Pinus jeffrey, Pinus resinosa, Pinus rigida, Pinus banksiana, Pinus serotina, Pinus strobus, Pinus monticola, Pinus lambertiana, Pinus virginiana, Pinus contorta, Pinus cariboea, Pinus pinaster, Pinus brutia, Pinus eldarica, Pinus coulteri, Pinus nigra, Pinus sylvestris, Pinus tecunumannii, Pinus keysia, Pinus oocarpa* and *Pinus maxinumoii*, and hybrids between the above species.

The constructs can also be used to transform other plants such as trees selected from *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoiasempervirens, Taxodium distichum, Tsuga canadensis, Tsuga heterophylla, Tsuga mertensiana, Thuja occidentalis, Thuja plicata;* Eucalypts, such as *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus novaanglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids between any of the above species.

As discussed above, transformation of a plant with a DNA construct including an open reading frame coding for a peptide wherein the open reading frame is orientated in a sense direction can, in some cases, lead to a decrease in expression of the peptide by co-suppression. Transformation of the plant with a DNA construct comprising an open reading frame in an anti-sense orientation or a non-coding (untranslated) region of a gene will lead to a decrease in the expression of the peptide in the transformed plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed.

Once the cells are transformed, cells having the DNA construct incorporated into their genome may be selected by means of a marker, such as the NPT II or kanamycin resistance markers discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initation medium is employed. For explants, an appropriate regeneration medium is used.

For a review of regeneration of forest trees such as those of the *Pinus* genus, see Dunstan et al., Somatic embryogenesis in woody plants. In: Thorpe, T. A. ed. 1995: in vitro embryogenesis of plants. Vol 20 in Current Plant Science and Biotechnology in Agriculture, Chapter 12, pp. 471–540.

The promoter, and constructs containing it, are not restricted in use to plants of forestry species. They can also be used to transform other agronomically important plants in which modulation of reproductive capacity (particularly the timing and abundance of flowering) is desirable. Such plants include cereals, rice, maize, wheat, barley, oats, rye, soyabean and canola.

The resulting transformed plants may be reproduced sexually or asexually, using methods well known in the art, to give successive generations of transgenic plants.

The invention will now be described with reference to the following non-limiting examples.

EXPERIMENTAL

Section 1

1. PrAG1 cDNA Cloning:

Total RNA was purified from immature cone of radiata pine according to the protocol of Charles Ainsworth (Plant Molecular Biology Reporter, 12(3), 1994: 198–203). The mRNA was isolated with oligo-T cellulose column. With mRNA as template, the cDNA was synthesised with CapFinder cDNA synthesis kit (ClonTech Co.). The cDNA was inserted into Lambda TriplEx Vector (ClonTech Co.), then packaged it with Gigapack@ III packaging extracts (Stratagene Co.) to obtain a cDNA library.

Two degenerate primers were designed:

3' PCR primer: 5' GCIGTIAGIYCITCICCCAT 3'; (SEQ ID NO:7)

5' PCR primer: 5' AAYCGICARGTIACITT 3' (SEQ ID NO:8)

These primers were used to perform RT-PCR based differential screening on RNA from various female tissue sources, including immature female buds, vegetative tissue from needles and later stages of development. The 50-ul reaction mixture contained 2.5 Units Taq DNA polymerase, 1× Polymerization Buffer (both from ClonTech Co.), 1 mMMgCl$_2$, 0.2 mMdNTP and 0.25 uM primers. The PCR was performed under the following conditions: denaturation at 94° C. for 30 s, annealing at 50° C. for 1 min and extension at 72° C. for 1 min for 30 cycles on a Thermal Cycler 480 (Perkin-Elmer, Norwalk, Conn., USA).

Fragments were obtained mostly from immature female bud tissue RNA samples. Several DNA fragments were cloned into pGEM-T vector and sequenced. Sequence analysis showed that most of these fragments contained similar sequences. One of the DNA fragments (309 bp) was chosen. This was used as a probe to screen the cDNA library to clone its full-length cDNA and resulted in the cDNA clone, PrAG1. The sequence of PrAG1 was analysed on both strands by the Sanger's dideoxy method (Sanger et al., 1977, Proc. Natal. Acad. Sci. U.S.A. 74: using a Sequenase kit (United States Biochemical co.).

The resulting sequence is shown in FIG. 1 gives the nucleotide sequence coding for the peptide of the invention together with the predicted amino acid sequence.

Sequence comparison and phylogenetic analysis were conducted with the software program MacDNASIS (Version 3.5, Hitachi Corp.). The results of analysis revealed PrAG1 to be a MADS box gene.

2. PrAG1 Promoter Cloning:
I. Genomic DNA Purification:

Genomic DNA was purified from young needles according to a CTAB method as described below.

1) 2 g of young needles of *Pinus radiata* were ground in liquid nitrogen (mortar and pestle) to a fine powder.

2) This powder was mixed with 15 mL of pre-warmed CTAB extraction buffer [3% CTAB (W/V), 100 mM Tris-HCl pH8.0, 20 mM EDTA pH8.0, 1.4 M NaCl, 1% PVP 940,000, 1% beta mercaptoethanol] and incubated at 65° C. for one hour.

3) To the above mixture 15 mL chloroform was added and mixed gently.

4) The contents were centrifuged at 10,000 g for 20 minutes at 4° C.

5) The supernatant was transferred to a new tube, and mixed with ⅒ volume of 3M sodium acetate (pH4.8), and 0.7 volume of isopropanol. The DNA was precipitated at −20° C. for 30 minutes.

6) The DNA was pelleted at 10,000 g for 10 minutes at 4° C.

7) The DNA pellet was then air dried and resuspended in 2 mL TE buffer (10 mM Tris-HCl pH7.5, 1 mM EDTA pH8.0) and 2,&1 of RNAse A (10 $\mu g/\mu L$) was added. The contents were incubated at 37° C. for 30 minutes to remove any RNA from the sample.

8) After the incubation, 2 mL of 5M Ammonium acetate and 10 mL of 100% ethanol were added and the contents kept at −20° C. for 15 minutes.

9) The mixture was then centrifuged at 10,000 g for 10 minutes at 4° C. to pellet DNA. The DNA pellet was washed in 70% ethanol twice.

10) The DNA pellet was air dried and resuspended in 200 uL TE bufffer.

II. Cloning of PrAG1 Promoter with Two Step Genomic DNA Walking.

1) The Universal Genome Walker Kit (CLONTECH) was employed. For the first step genomic DNA walking, two PrAG1 specific primers were designed and synthesized according to the PrAG1 cDNA sequence. The sequences of the primers were:

Primer GSP1: 5∝ CGC CTT CTT CAA TAA ACC ATT TCG GCG CTT 3' (SEQ ID NO:9)

Primer GSP2: 5' GAC CTG TCG GTT COT AGT ATT TTC AAT CCT 3' (SEQ ID NO: 10)

2) Based upon the promoter sequence we got from step 1), two PrAG1 promoter sequence specific primer were designed and synthesized. The primers were:

Primer GSP3: 5' TTC GTC CTC CAT TTT GTG CGC TCT CCA TTC 3' (SEQ ID NO:11)

Primer GSP4: 5' GCA CTC CAC TCT TCC TTT ATT TCT TAC CAC 3' (SEQ ID NO:12)

3) According to the User Manual of Universal Genome Walker Kit, 13 genome walker libraries were constructed after genomic DNA digestion with restriction enzymes: EcoR V, Sca I, Dra I, Pvu II, Ssp I, Stu I, Sma I, Hap I, BsaB I, Bcl136 II, Pml I, Nru I, Hic II.

4) With 13 genome walker libraries as templates, and adaptor primer 1 (AP1 primer from kit) and GSP1 primer, first round PCR was performed under the conditions suggested by the kit manufacturer. After agarose electrophoresis analysis of the PCR product, second round PCR was performed with the nested primers AP2 (Adaptor primer from the kit) and GSP2. The PCR products from the second round PCR were purified and cloned into pGEM-T easy vector (Promega). Following sequence analysis, and DNA sequence comparison with PrAG1 cDNA, one DNA fragment of 1105 bp from Sca I genome walker library was obtained which was identified as the promoter region of PrAG1, based upon the overlapped region between it and PrAG1 cDNA.

5) The second step genome walking was done with primer pair AP1 and GSP3, and primer pair AP2 and GSG4. A DNA fragment of 449 bp from the Dra I genome walker library was identified as the upstream sequence of the PrAG1 promoter cloned from the first step genome walking based on the sequence comparison of overlapped region between them.

6) The 1105 bp and 449 bp fragments were used in PCR mediated DNA splicing to synthesize one continuous 1458 pb promoter fragment of PrAG1. This was done as described. One primer was synthesized based on the 5'end sequence of 1105 bp promoter fragment: Primer PLi, 5' AGT TAC TTA ACA ATG CGC MC CAA GGC 3' (SEQ ID NO. 13). Primer pair PLi and GSP2 was used in PCR to get the promoter fragment of 1105 pb, in which the AP2 primer sequence was removed. This 1105 bp fragment and 449 bp fragment was then added in one PCR tube as a template with the primer pair of AP2 and GAP2 to do the second round PCR to get the 1458 bp PCR fragment. The conditions of second round PCR were as follows: the first cycle at 95° C. for 5 minutes, and 68° C. for 10 min; the second cycle at 94° C. for 30 seconds (DNA denaturing), DNA annealing at 60° C. for 1 min, and DNA synthesis at 72° C. for 2 minutes; this regime was cycled 30 times. This 1458 bp fragment was then cloned into pGEM-T easy vector (Promega) and subjected to DNA sequencing on both strands to confirm the DNA sequence and to make sure that no base changes occurred during the PCR process.

The sequence of the promoter, (which is the PrAG1 promoter), is given in FIG. 2 from nucleotides 1 to 1320.

7) DNA sequence analysis has indicated that compared to its orthologs from other plants, the PrAG1 showed that there were two possible positions for transcription initiation: at position 791 or 1326 in the FIG. 2 sequence. It was found three typical TATA boxes in the PrAG1 promoter at the position of 280 to 286, 282 to 288, 1015 to 1021. Based on the start codon position and short 5' untranslated region in the PrAG1 cDNA, the transcription initiation point is identified as position 1326 in the FIG. 2 sequence.

3. DNA and RNA Gel Blot Hybridizations:

Genomic DNA and RNA gel blots were made using standard techniques (Sambrook et al., 1989. Molecular Cloning: A Laboratory Cold Spring Harbor, N.Y.: Cold Spring Harbor Laboratory Press).

RNA: Total RNA was prepared from needle, vegetative shoot, stem, immature female cone and immature male cone samples as described above. Briefly, 20 µg of total RNA was denatured in formaldehyde loading buffer and fractionated by denaturing agarose gel electrophoresis on a formaldehyde containing gel. The agarose gel was stained with ethidium bromide and a picture taken as control. The RNA was then transferred to a nylon membrane by the capillary blotting method. The RNA was immobilised on the membrane by UV cross-linking and was prehybridized at 65° C. for 2 hours prior to hybridization in 0.5M Na-phosphate, pH 7.2, 7.5% SDS, 1 mM EDTA, 100 ug/mL salmon sperm DNA. A DNA fragment of PrAG1 3' end region was labelled with $^{32}P\_dCTP$ (Decaprime B kit, Ambion, Austin, Tex.), and hybridised to the RNA blot overnight at 65° C. The blot was washed twice in 40 mMNa-PO4, 1% SDS and 1 mM EDTA for 30 minutes each at 65° C., and exposed to X-ray film with intensifying screens at 80° C.

DNA: Genomic DNA was prepared from needle tissue with CTAB method. Twenty µg genomic DNA was digested by Bam HI, Bgl II, Eco RI, Hin III and Xba I respectively. After agarose gel running, alkali blotting of DNA to Hybond N membranes was performed as described by the manufacturer (Amersham). The probe hybridisation and washing was as described for the RNA blotting analysis.

Figure 4:
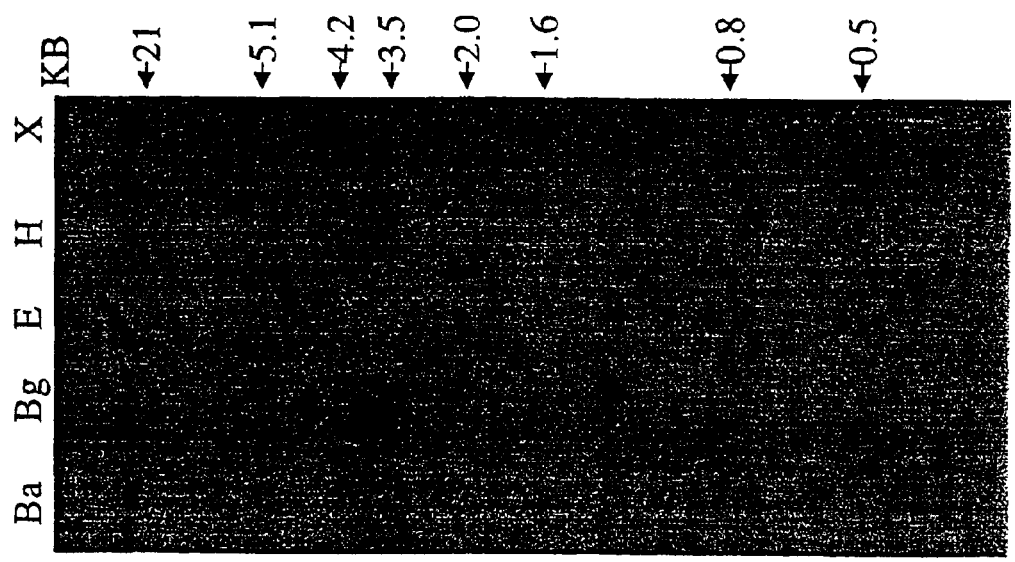
FIG. 4 is a DNA gel blot analysis of *Pinus radiata* genomic DNA hybridized with the 3' terminal region of PrAG1. 20 µg genomic DNA was digested with BamHI (BA) and Bgl II (BG) EcoRI (E), HindIII (H), XhoI (X)

The results are shown in FIGS. 3 and 4.

4. RT-PCR:

Analysis was performed on total RNA isolated from needle, stem, vegetative shoot, immature female cone and immature male cone samples as described above. RNA was reverse-transcribed with MMLV reverse-transcriptase (Gibco BRL) according to the manufacturer's instructions. PCR was performed with two primers: 5'PCR primer (5' TTGTGTACAAATCATGGG 3') (SEQ ID NO:14) and 3'PCR primer (5'GTAAGCCCGTCACCCATC 3' ) SEQ ID NO: 15). Verification of the specificity of the PCR reactions was achieved through the use of controls that included amplification reaction with single primers, RNAse treatment of template, and no template. In those reactions in which no PCR product was detected, the quality of the RNA was tested by UV scanning and agarose gel electrophoresis. ss-cDNA from the RT reaction was used as a template. The 50-ul reaction mixture contained 2.5 U Taq DNA polymerase, 1× Polymerization Buffer (both from ClonTech Co.), 1 mM $MgCl_2$, 0.2 mM dNTP and 0.25 µM primers. The PCR was performed under following conditions: denaturation at 94° C. for 30 s, annealing at 55° C. for 1 min and extension at 72° C. for 1 min for 30 cycles on Thermal Cycler 480 (Perkin-Elmer, Norwalk, Conn., USA). The PCR products were subjected to electrophoresis in agarose gel and hybridization as described above.

Figure 5:
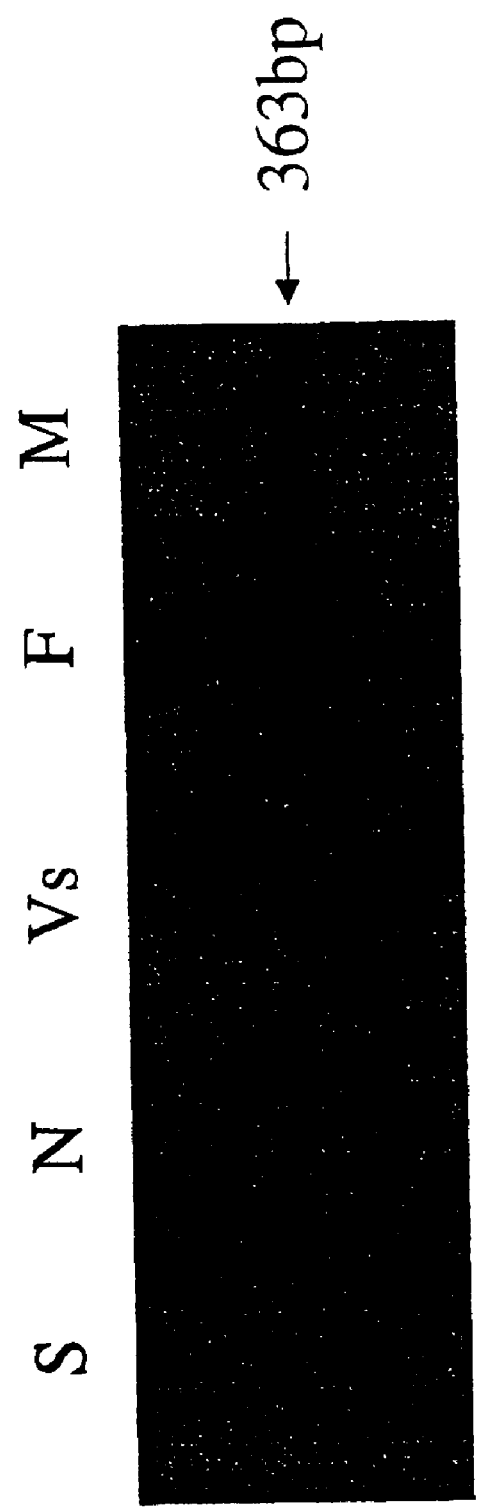
FIG. 5 is a Reverse Transcription-Polymerase Chain Reaction (RT-PCR) analysis showing reproductive-organ specific expression of PrAG1. RT-PCR analysis was performed on total RNA isolated from different organs of radiata Pine: (M) immature male cone, (F) immature female cone, (Vs) vegetative shoot, (N) needle and (S) stem. MADS box genes were amplified with PrAG1 gene-specific oligonucleotides. Products from the PCR reactions were electrophoresed, blotted, and hybridized with a labelled probe of PrAG1 specific fragment; from the PCR reactions were electrophoresed, blotted, and hybridized with a labelled probe of PrAG1 specific fragment.

The results are shown in FIG. 5.

Discussion

Northern blot hybridization and RT-PCR analysis showed that PrAG1 mRNA is accumulated specifically in the immature female cone and immature male cone; there is no expression detected in needle, stem, and vegetative shoot (FIGS. 3 and 5). This tissue distribution profile, when combined with the fact that PrAG1 contains a MADS box, verifies that PrAG1 is a reproductive gene in *Pinus radiata* and that the PrAG1 promoter is reproductive-tissue specific.

Southern blot analysis showed that PrAG1 gene exists as a single copy in the genome of *Pinus radiata* (FIG. 4).

Section 2

Figure 6:
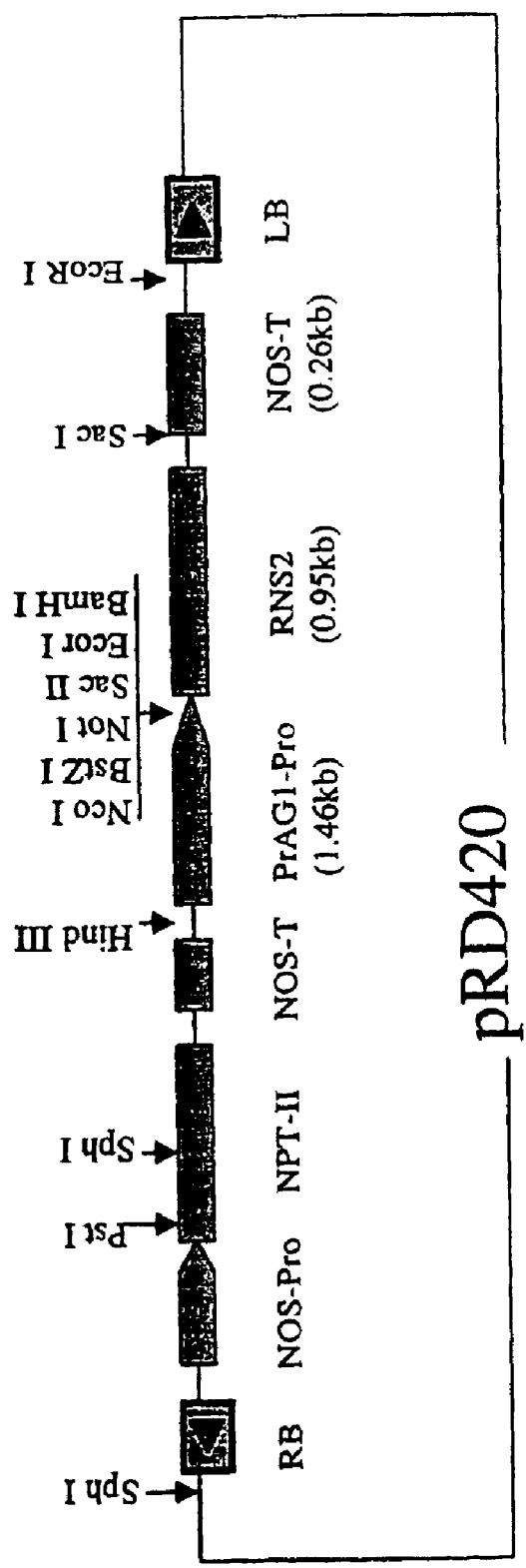
FIG. 6 shows the construction of pRAGPR.

Construction of Binary Vector pRAGPR, Plant Transformation and Regeneration f Transgenic Tobacco Plants A DNA fragment containing the PrAG1 promoter (1.40 kb, SEQ ID NO:2) operably fused to an RNAse gene (0.95 kb, RNS2, Taylor et al. *Proc Natl Acad Sci*, USA 90 (11), 5118–5122 (1993)) and containing Hind III and Sac I sites was gel purified and ligated into the Hind III/Sac I sites of binary vector pRD420, containing the NPTII gene for plant selection, (provided by Dr. R. S. S. Datla, PBI, Saskatoon, Canada) resulting in the construct pRAGPR (FIG. 6). The construct was introduced into *Agrobacterium tumefaciens* (strain c58 MP90), and used to transform and regenerate *Nicotiana tabacum* var. *Xanthi* by the standard leaf disc transformation ethod (Horsch et al. (1985), A simple and general method for transferring genes into plants. *Science* 227, 1229–1231). Control lines were also generated through leaf disk method without the selection process. After kanamycin selection, the putative transgenic plantlets were rooted in the rooting medium containing kanamycin and then moved to pots containing the Metromix 350 potting mix. Potted plants were maintained under controlled conditions in a growth chamber with 16 h photoperiod. The plants were grown through the full life cycle of the tobacco until senescence and the flowering of the transgenic tobacco assessed relative to controls. Transgenic plants were identified further by PCR with template of genomic DNA and Southern blot analysis to confirm the integration of pRAGPR in transgenic tobacco plants.

Polymerase Chain Reaction Amplification

To check the genomic DNA integration of pRAGPR in the transgenic tobacco plants, gene-specific primers for the NPTII gene were employed. The primers used were NPTII-5' primer 5-GAA CAA GAT GCA TTG CAC GC-3' (SEQ ID NO: 16) and NPTII-3' primer 5'-GAA GAA CTC GTC AAG AAG GC-3' (SEQ ID NO: 17). Genomic DNA from each of the control lines and transgenic tobacco lines were isolated from the leaf tissue using the Qiagen DNAeasy kit as per manufacturer's instructions. PCR reactions (50-µl final volume) were performed using 5 µl of template DNA. Samples were heated to 95° C. for 4 minutes, followed by 35 cycles of 95° C. for 45 seconds, 55° C. for 30 seconds, and 73° C. for 2 minutes, with a final extension step of 73° C. for 5 minutes in PTC100 thermal cycler (MJ Research). Amplified DNA fragments were analyzed on a 0.8% agarose gel and visualized by staining with ethidium bromide.

DNA Gel Blot Hybridization

To confirm the genomic integration of PrAG1 promoter-RNAse gene cassette in transgenic plants and to determine the copy number, Southern analysis was performed. For Southern analysis, genomic DNA (20 µg) was digested with appropriate restriction endonucleases, separated by electrophoresis in a 0.8% agarose gel. Two sets of Southerns were performed, one with digesting the genomic DNA with Hind III and Sac I to drop the PrAG1-RNAse cassette and another with Hind III digest alone to test for integration profiles. Following depurination in 0.25 M HCl and denaturation in 0.5 M NaOH, 1.5 M NaCl, the DNA was blotted onto a nylon membrane. The RNAse gene-specific probe (which is the whole RNAse gene) was radioactively labelled using a random-primed DECAprime II DNA labeling kit (Ambion, Austin, Tex.). Filters were hybridized at 65° C. in a hybridization buffer containing 0.5 M NaPO$_4$ (pH 7.5), 7.5% SDS, and 1 mM EDTA. All filters were washed finally at 68° C. in 20 mM NaPO$_4$ (pH 7.5), 1% SDS. Filters were then subjected to autoradiography.

Results and Conclusions

Transgenic Tobacco Plants Expressing PrAG1 Promoter Controlled RNAs Gene.

Figure 7:
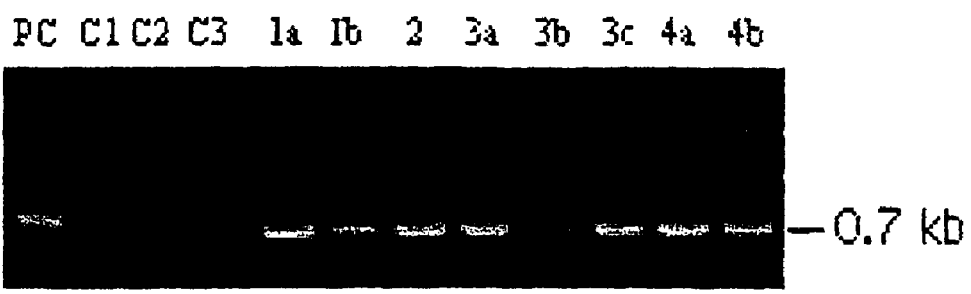
FIG. 7. PCR analysis of transgenic tobacco lines. Genomic DNA (200 ng each) from controls and putative transgenic tobacco plants was used as template along with primers for NPTII gene. Lane PC is positive control (20 ng pRAGPR plasmid was used as a template); C1–C3 are control nontransformed tobacco plants; lanes 1a, 1b, 2, 3a, 3b, 3c, 4a, 4b are transgenic plants. The size of NPT II gene PCR product is indicated on the right.

Eight independent transgenic lines of tobacco (*N. tobaccum* var *Xanthi*) with the PrAG1-RNAse fusion construct were obtained together with three control lines processed through the same tissue culture propagation method but without the selection. PCR was done on the putative transgenic plantlets, after rooting in selection medium, to confirm the integration of the NPTII gene. All the eight lines were positive for the NPTII gene and the controls were negative (FIG. 7). The transgenic plants were propagated in pots along with the controls.

Figure 8:
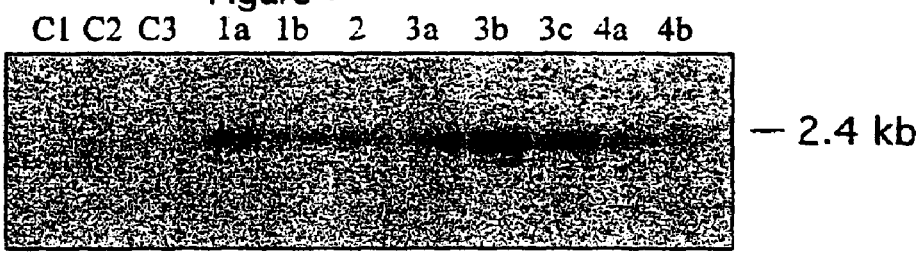
FIG. 8. Southern analysis of transgenic and control tobacco lines to confirm integration of PrAG1 promoter-RNAse gene cassette. Genomic DNA (20 ug each) was digested with Hind III and Sac I enzymes, electrophoresed and transferred to a nylon membrane. $^{32}$-p labeled RNAse gene was used as a probe. The size of PrAG1 promoter-RNAse gene cassette is indicated on the right. Designation of control and transgenic plants is as indicated in FIG. 7.

Southern analysis was done on the eight transgenic lines and the three controls to confirm the integration and profiles of integration of PrAG1 promoter-RNAse gene cassette. Double digestion with Hind III and Sac I followed by probing with RNAse gene probe indicated that all the eight transgenic plants had the PrAG1-RNAse cassette (FIG. 8). The single digest with Hind III indicated that 5 of the transgenic lines had single integration and three others had two copies of the cassette.

Out of the 5 transgenic plants with single integration two profiles were found based on molecular weight size bands that hybridized to the RNAse probe. Three plants had the same size band hybridizing at ~4 kb (#s 3a, 3 c, 4a) whereas, the two other plants had a band hybridizing at ~3 kb range (#s 3b, 4b)(FIG. 9).

Figure 9:
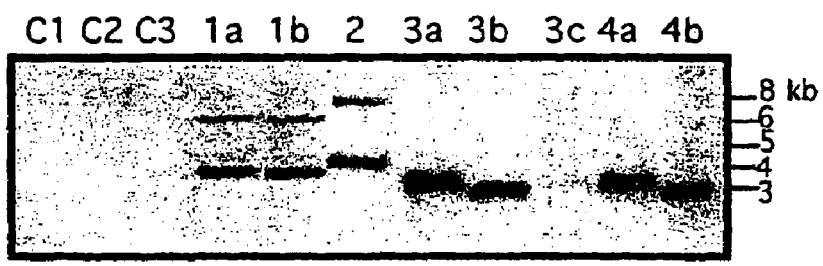
FIG. 9. Southern analysis of transgenic and control tobacco lines to confirm integration profiles of PrAG1 promoter-RNAse gene cassette. Genomic DNA (20 ug each) was digested with Hind III enzyme, electrophoresed and transferred to a nylon membrane. $^{32}$-P labeled RNAse gene was used as a probe. Sizes of DNA fragments hybridizing to the RNAse gene probe are indicated on the right. Designation of control and transgenic plants is as indicated in FIG. 7.

Of the three transgenic plants that had two copies of the cassette, two had same profile with a band at 5–6 kb and another at 4 kb hybridizing to the RNAse probe (#1a, 1b), whereas the other had two bands, one at 8 kb and another at 4 kb that hybridized to RNAse probe (#2) (FIG. 9).

All the three controls were negative for hybridization with the RNAse probe (FIG. 8 and FIG. 9).

Reproductive Sterility in Transgenic Tobacco Caused by pRAGPR.

All the controls and transgenic lines were allowed to senesce (approximately 3 months). The controls flowered normally whereas none of the transgenic tobacco containing the pRAGPR construct flowered. The plants with single copy PrAG1-RNAse cassette grew at the same rate as controls and senesced at the same time. The transgenic plants with two copies of pRAGPR were slower to grow, and matured late (#1a, 1b and 2).

All transgenic plants eventually died and none flowered.

Another phenotypic change observed was in transgenic line #2, which developed additional lateral branches near the top. This may be due to the lack of or decreased apical dominance in these plants. Thus, the inhibition of flowering using the PrAG1-RNAse cassette may have an added benefit to increase the biomass of the plant through increased branching if the growing conditions are not limiting.

Industrial Application

In its primary aspect, the invention provides a new, reproductive-tissue-specific promoter. This promoter can be used in transforming a wide variety of plants. The promoter can also be used to drive expression of any gene which it is desirable to express in plant reproductive organs, including flowering time genes.

The invention also has application in modulating, and in particular reducing or eliminating reproductive capacity in plants including those of the *Pinus* genus and *Eucalyptus* genus. Such plants have utility in forestry.

The availability of reproductively null or sterile pine or eucalyptus trees has the additional advantage that it will be possible to introduce further exogenous genetic material into those trees without the risk that the material will be passed on to other trees.

Those persons skilled in the art will appreciate that the specific description provided is exemplary only, and that modifications and variations may be made without departing from the scope of the invention.

What is claimed is:

1. An isolated polynucleotide which has the nucleotide sequence of SEQ ID NO. 1 and which has the ability, when operably associated with a further nucleotide sequence encoding a peptide, to promote transcription of said further nucleotide sequence, or an isolated polynucleotide which has at least 95% nucleotide sequence identity to SEQ ID NO. 1 and which is a functionally equivalent variant of SEQ ID NO. 1.

2. An isolated plant reproductive tissue specific promoter which has the nucleotide sequence of SEQ ID NO. 1 or a functionally equivalent variant thereof which has at least 95% nucleotide sequence identity with SEQ ID NO. 1.

3. An isolated plant reproductive tissue promoter which has the nucleotide sequence of SEQ ID NO. 2.

4. A DNA construct which comprises as operably linked components:
   (a) a polynucleotide having activity as a transcriptional promoter according to claim 1;
   (b) an open reading frame polynucleotide coding for a peptide; and
   (c) a termination sequence.

5. A DNA construct which comprises as operably linked components:
   (a) a promoter sequence as given in SEQ ID NO. 1 or a functionally equivalent variant thereof which has at least 95% homology to SEQ ID NO. 1 or a promoter sequence as given in SEQ ID NO. 2;
   (b) an open reading frame polynucleotide coding for a peptide; and
   (c) a termination sequence.

6. The construct as claimed in claim 4 or claim 5 in which the open reading frame is in a sense orientation.

7. The construct as claimed in claim 4 or claim 5 in which the open reading frame is in an anti-sense orientation.

8. The construct according to claim 5 wherein said open reading frame encodes a peptide having SEQ ID NO. 4.

9. The construct according to claim 6 wherein said open reading frame polynucleotide encodes a peptide which, when expressed in reproductive tissue of a plant, causes said plant's reproductive organs to abort.

10. The construct according to claim 6 wherein said open reading frame polynucleotide encodes a peptide which, when expressed in reproductive tissue of a plant, causes said plant's reproductive organs to redefine themselves as vegetative.

11. The construct according to claim 6 wherein said open reading frame polynucleotide encodes a peptide which, when expressed in reproductive tissue of a plant, causes said plant's reproductive organs to stop development.

12. The construct according to claim 6 wherein said open reading frame polynucleotide encodes a peptide which, when expressed in reproductive tissue of a plant, causes cell death.

13. The construct according to claim 12 wherein the peptide which causes cell death is selected from the group consisting of diphtheria toxin A and Barnase.

14. The construct according to claim 12 wherein the peptide which causes cell death is an RNAse.

15. The construct according to claim 14 wherein said RNase is encoded by the nucleotide sequence of SEQ ID NO. 5.

16. The construct according to claim 6 wherein said open reading frame polynucleotide encodes a peptide which, when expressed in reproductive tissue of a plant, causes an alteration in the timing of flowering of said plant.

17. The construct according to claim 5 which further includes:
   (d) a selection marker sequence.

18. The construct according to claim 17 in which said selection marker sequence is the NPTII gene.

19. A transgenic plant cell which includes a construct according to claim 5.

20. A transgenic plant which includes a construct according to claim 8.

21. A transgenic plant which contains a polynucleotide according to claim 1 or a promoter according to claim 5, which plant has a reduced reproductive capacity.

22. The transgenic plant according to claim 21 wherein in said plant said polynucleotide or said promoter is operatively associated with a nucleotide sequence encoding a peptide, which when expressed in reproductive tissue of the plant, causes the plant's reproductive organs to abort, redefine as vegetative or stop development.

23. The transgenic plant according to claim 21 wherein in said plant said polynucleotide or promoter is operatively associated with a nucleotide sequence encoding a RNAse.

24. The transgenic plant according to claim 23 in which the RNAse has the sequence of SEQ ID NO. 6.

25. The transgenic plant according to claim 20 wherein said plant is a coniferous plant.

26. The transgenic plant according to claim 25 which is a coniferous plant of the *Pinus* genus.

27. The transgenic plant according to claim 26 which is a member of a species selected from the group consisting of *Pinus radiata, Pinus taeda, Pinus elliotti, Pinus clausa, Pinus palustrus, Pinus echinata, Pinus ponderosa, Pinus jeffrey, Pinus resinosa, Pinus rigida, Pinus banksiana, Pinus serotina, Pinus strobus, Pinus monticola, Pinus lambertiana, Pinus virginiana, Pinus contorta, Pinus cariboea, Pinus pinaster, Pinus brutia, Pinus eldarica, Pinus coulteri, Pinus nigra, Pinus sylvestris, Pinus tecunumannii, Pinus keysia, Pinus oocarpa* and *Pinus maxinumoii*; and hybrids between any of the above species.

28. The transgenic plant according to claim 20 wherein said plant is a tree.

29. The transgenic plant according to claim 28 which is a member of the *Eucalyptus* genus.

30. The transgenic plant according to claim 26 which is a member of a species selected from the group consisting of *Eucalyptus alba, Eucalyptus bancroftii, Eucalyptus botyroides, Eucalyptus bridgesiana, Eucalyptus calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurii, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo* and *Eucalyptus youmanni*; and hybrids between any of the above species.

* * * * *

UNITED STATES PATENT AND TRADEMARK OFFICE
CERTIFICATE OF CORRECTION

PATENT NO.    : 6,858,776 B1
DATED         : February 22, 2005
INVENTOR(S)   : Podila et al.

It is certified that error appears in the above-identified patent and that said Letters Patent is hereby corrected as shown below:

Column 2,
Line 33, delete "*cause,*" and replace with -- *clausa* --.

Column 9,
Line 53, delete "2,&I" and replace with -- 2 µl --.

Column 10,
Line 4, delete "5$^{\propto}$" and replace with -- 5' --.
Line 6, delete "COT" and replace with -- CGT --.
Line 51, delete "GAP2" and replace with -- GSP2 --.

Column 11,
Line 28, delete "80° C." and replace with -- -80° C. --.
Line 31, delete "Hin III" and replace with -- Hind III --.

Column 12,
Line 9, delete "f" and replace with -- of --.
Line 21, delete "ethod" and replace with -- method --.
Line 40, delete "GAT GCA" and replace with -- GAT GGA --.

Column 30,
Line 43, delete "claim 26" and replace with -- claim 29 --.

Signed and Sealed this

Thirtieth Day of August, 2005

JON W. DUDAS
*Director of the United States Patent and Trademark Office*

SEQUENCE LISTING

```
<160> NUMBER OF SEQ ID NOS: 17

<210> SEQ ID NO 1
<211> LENGTH: 1320
<212> TYPE: DNA
<213> ORGANISM: Pinus radiata

<400> SEQUENCE: 1
aaactcgaca gcaaatatga tttagattat gacctagaaa taagcatagc attaaagcat      60
atacataaca agcggtgata tactctgact gccactgtac ttgaggaaag gtagtggact     120
ctgctcaggt acattagttt ggtaaggttg gcttggcttc tgggtaatat gagaagtaaa     180
gaagtaaaag gtatttgact ctagtcaagt acattggatt gcctttgtcg gggcttggat     240
ggcttgggtt cgtgtgagaa gccaacaatt tataagaaat atataaaata aaaaataaaa     300
aaatttaagt gttggaagtg aaaacggtgg ggcagaaata tacacagaag agtactttaa     360
caatgcgcaa ccaaggcaga ttcacaactt gatttctgga cctcgaatac gagataatgg     420
tggtaagaaa taaaggaaga gtggagtgca tttgaaaatg aatggagagc gcacaaaatg     480
```

-continued

```
gaggacgaat aaatgaaata taatgcaaga gtgcatttcc ctattatttc cagaaatgta      540
tatgtggggt cggcattcac atgggcgtcg cattcagggg gtgtcatagc ggtcctttga      600
ttgcagtgtg ggagttgcaa catgtaccaa caaatccatt catcccaaaa cctaaattta      660
tcctctccat tactattacc tacacctata cctagtaaat atgtcctgcc ttgtaactcc      720
tccactgcct gcacacgtct tagtcaatcc atctgccttc aaataggcat tattttgttc      780
tttcccctcc gactgaaagg ctatcgaccg accgaccgct catcttcttc ttctgcgcaa      840
ttttttctgc tggatcatca tcattaccat catcgccatc cccaccatca tcatcatgat      900
ggtatctcta tctctccctg gcaatcgatt gtagaggaaa ggaagaggga agggcatat      960 gtattgatca acctacccga aaaacaatc tgatcagccc tgctcaatct tgcttataaa     1020
tctcttatcc actgttcaat cattcaggtt cttcccact ttcaagcaaa ggcgcccgga     1080
ttggccgtgt tcttagattt tcaggtactt aaatggacaa tattccccac ctgaagccgt     1140
tctgaaaaag atttgtttgt agaaacaaac gattgtaata tttgcttaag ttgagcttaa     1200
ggggtttggt acctaacttg ccttgtggtt atttgtttct cagaactcgg ctgcgtcca     1260 actgtaggaa cgaaccagca caaggggttg cagcttttgc tgttgctgtt gcgcccattg     1320
```

<210> SEQ ID NO 2
<211> LENGTH: 1401
<212> TYPE: DNA
<213> ORGANISM: Pinus radiata

<400> SEQUENCE: 2

```
aaactcgaca gcaaatatga tttagattat gacctagaaa taagcatagc attaaagcat       60
atacataaca agcggtgata tactctgact gccactgtac ttgaggaaag gtagtggact      120
ctgctcaggt acattagttt ggtaaggttg gcttggcttc tgggtaatat gagaagtaaa      180
gaagtaaaag gtatttgact ctagtcaagt acattggatt gcctttgtcg ggcttggat      240 ggcttgggtt cgtgtgagaa gccaacaatt tataagaaat atataaaata aaaataaaa      300 aaatttaagt gttggaagtg aaaacggtgg ggcagaaata tacacagaag agtacttaa      360 caatgcgcaa ccaaggcaga ttcacaactt gatttctgga cctcgaatac gagataatgg      420
tggtaagaaa taaggaaga gtggagtgca tttgaaaatg aatggagagc gcacaaaatg      480
gaggacgaat aaatgaaata taatgcaaga gtgcatttcc ctattatttc cagaaatgta      540
tatgtggggt cggcattcac atgggcgtcg cattcagggg gtgtcatagc ggtcctttga      600
ttgcagtgtg ggagttgcaa catgtaccaa caaatccatt catcccaaaa cctaaattta      660
tcctctccat tactattacc tacacctata cctagtaaat atgtcctgcc ttgtaactcc      720
tccactgcct gcacacgtct tagtcaatcc atctgccttc aaataggcat tattttgttc      780
tttcccctcc gactgaaagg ctatcgaccg accgaccgct catcttcttc ttctgcgcaa      840
ttttttctgc tggatcatca tcattaccat catcgccatc cccaccatca tcatcatgat      900
ggtatctcta tctctccctg gcaatcgatt gtagaggaaa ggaagaggga agggcatat      960 gtattgatca acctacccga aaaacaatc tgatcagccc tgctcaatct tgcttataaa     1020
tctcttatcc actgttcaat cattcaggtt cttcccact ttcaagcaaa ggcgcccgga     1080
ttggccgtgt tcttagattt tcaggtactt aaatggacaa tattccccac ctgaagccgt     1140
tctgaaaaag atttgtttgt agaaacaaac gattgtaata tttgcttaag ttgagcttaa     1200
ggggtttggt acctaacttg ccttgtggtt atttgtttct cagaactcgg ctgcgtcca     1260 actgtaggaa cgaaccagca caaggggttg cagcttttgc tgttgctgtt gcgcccattg     1320
```

```
ctttttggact ggtattagta gttgcagctt tgttttgcat acgctgtgag gatctgtgcg    1380
cggaaatttt gtgtacaaat c                                              1401
```

<210> SEQ ID NO 3
<211> LENGTH: 909
<212> TYPE: DNA
<213> ORGANISM: Pinus radiata
<220> FEATURE:
<221> NAME/KEY: CDS
<222> LOCATION: (1)..(669)
<223> OTHER INFORMATION: Pinus radiata MADS box protein mRNA, complete cds
<300> PUBLICATION INFORMATION:
<301> AUTHORS: Jun-Jun, Liu
      Podila, G K.
<302> TITLE: Not applicable
<303> JOURNAL: Direct submission
<304> VOLUME: -
<305> ISSUE: -
<306> PAGES: ---
<307> DATE: 1997-09-09
<308> DATABASE ACCESSION NUMBER: Genbank AF023615
<309> DATABASE ENTRY DATE: 1999-01-26
<313> RELEVANT RESIDUES: 1 TO 909

<400> SEQUENCE: 3

```
atg ggt cgt ggg aag att gag ata aag agg att gaa aat act acg aac    48
Met Gly Arg Gly Lys Ile Glu Ile Lys Arg Ile Glu Asn Thr Thr Asn
 1               5                  10                  15 cga cag gtc act ttc tgc aag cgc cga aat ggt tta tta aag aag gcg    96
Arg Gln Val Thr Phe Cys Lys Arg Arg Asn Gly Leu Leu Lys Lys Ala
             20                  25                  30 tat gaa tta tca gtt ctt tgt gat gca gaa gtg gcc ctc atc gtc ttc   144
Tyr Glu Leu Ser Val Leu Cys Asp Ala Glu Val Ala Leu Ile Val Phe
         35                  40                  45 tcc agc aga ggg aga ctt tat gaa ttt gcc aac cac agc gtg aag agg   192
Ser Ser Arg Gly Arg Leu Tyr Glu Phe Ala Asn His Ser Val Lys Arg
     50                  55                  60 acg att gag agg tac aag aag act tgc gtt gac aac aac cac gga ggg   240
Thr Ile Glu Arg Tyr Lys Lys Thr Cys Val Asp Asn Asn His Gly Gly
 65                  70                  75                  80 gcg ata tca gag tcc aat tct cag tat tgg caa cag gag gct ggt aaa   288
Ala Ile Ser Glu Ser Asn Ser Gln Tyr Trp Gln Gln Glu Ala Gly Lys
                 85                  90                  95 ctc aga caa cag att gac att ttg caa aat gca aat agg cat ttg atg   336
Leu Arg Gln Gln Ile Asp Ile Leu Gln Asn Ala Asn Arg His Leu Met
            100                 105                 110 ggt gac ggg ctt aca gct ttg aac att aag gaa ctc aag caa ctt gag   384
Gly Asp Gly Leu Thr Ala Leu Asn Ile Lys Glu Leu Lys Gln Leu Glu
        115                 120                 125 gtt cga ctt gaa aaa gga atc agc cga gtg cga tcc aaa aag aac gag   432
Val Arg Leu Glu Lys Gly Ile Ser Arg Val Arg Ser Lys Lys Asn Glu
    130                 135                 140 atg ttg ctt gaa gag atc gac atc atg cag aga agg gaa cac ata ctt   480
Met Leu Leu Glu Glu Ile Asp Ile Met Gln Arg Arg Glu His Ile Leu
145                 150                 155                 160 atc cag gag aat gag att ctt cgc agc aag ata gcc gag tgt cag aat   528
Ile Gln Glu Asn Glu Ile Leu Arg Ser Lys Ile Ala Glu Cys Gln Asn
                165                 170                 175 agc cac aac acg aac atg tta tca gct ccg gaa tat gat gca ctg ccc   576
Ser His Asn Thr Asn Met Leu Ser Ala Pro Glu Tyr Asp Ala Leu Pro
            180                 185                 190 gca ttc gac tct cga aat ttc cta cat gca aat cta atc gat gcg gcc   624
```

```
                            -continued

Ala Phe Asp Ser Arg Asn Phe Leu His Ala Asn Leu Ile Asp Ala Ala
        195                 200                 205 cat cac tat gca cat cag gaa caa aca acg ctt cag ctt ggc tga         669
His His Tyr Ala His Gln Glu Gln Thr Thr Leu Gln Leu Gly
        210                 215                 220 acgttgaagc ggtggacgct taaaactcaa tcaaggcacc cgaaaaatat gctagtaacc    729
ttgaatgaga ttcagagtcg aaatattgcg aggcaagagc acaatggaag agatagctcc    789
tagtatgaat atggatttat gatattaaca tatggtttgt cagcttaaa tatagctgtt    849 tgaaacaaag aatacaacat attagctagt attttttttgg cgcatgttat ctttctgttg   909

<210> SEQ ID NO 4
<211> LENGTH: 222
<212> TYPE: PRT
<213> ORGANISM: Pinus radiata

<400> SEQUENCE: 4

Met Gly Arg Gly Lys Ile Glu Ile Lys Arg Ile Glu Asn Thr Thr Asn
 1               5                  10                  15

Arg Gln Val Thr Phe Cys Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Arg Leu Tyr Glu Phe Ala Asn Ser His Ser Val Lys Arg
    50                  55                  60

Thr Ile Glu Arg Tyr Lys Lys Thr Cys Val Asp Asn His Gly Gly
65                  70                  75                  80

Ala Ile Ser Glu Ser Asn Ser Gln Tyr Trp Gln Gln Glu Ala Gly Lys
                85                  90                  95

Leu Arg Gln Gln Ile Asp Ile Leu Gln Asn Ala Asn Arg His Leu Met
            100                 105                 110

Gly Asp Gly Leu Thr Ala Leu Asn Ile Lys Glu Leu Lys Gln Leu Glu
        115                 120                 125

Val Arg Leu Glu Lys Gly Ile Ser Arg Val Arg Ser Lys Lys Asn Glu
    130                 135                 140

Met Leu Leu Glu Glu Ile Asp Ile Met Gln Arg Arg Glu His Ile Leu
145                 150                 155                 160

Ile Gln Glu Asn Glu Ile Leu Arg Ser Lys Ile Ala Glu Cys Gln Asn
                165                 170                 175

Ser His Asn Thr Asn Met Leu Ser Ala Pro Glu Tyr Asp Ala Leu Pro
            180                 185                 190

Ala Phe Asp Ser Arg Asn Phe Leu His Ala Asn Leu Ile Asp Ala Ala
        195                 200                 205

His His Tyr Ala His Gln Glu Gln Thr Thr Leu Gln Leu Gly
        210                 215                 220

<210> SEQ ID NO 5
<211> LENGTH: 1012
<212> TYPE: DNA
<213> ORGANISM: Arabidopsis thaliana
<220> FEATURE:
<221> NAME/KEY: CDS
<222> LOCATION: (16)..(795)
<223> OTHER INFORMATION: Arabidopsis thaliana ribonuclease (RNS2) mRNA,
      complete cds
<300> PUBLICATION INFORMATION:
<301> AUTHORS: Taylor, C B.
      Bariola, P A.
      delCardayre, S B.
```

Raines, R T.
Green, P J.
<302> TITLE: RNS2: a senescence-associated RNase of Arabidopsis that
diverged from the S-RNases before speciation
<303> JOURNAL: Proc. Natl. Acad. Sci. U.S.A.
<304> VOLUME: 90
<305> ISSUE: 11
<306> PAGES: 5118-5122
<307> DATE: 1993
<308> DATABASE ACCESSION NUMBER: Genbank
<309> DATABASE ENTRY DATE: 1994-10-30
<313> RELEVANT RESIDUES: 1 TO 1012

<400> SEQUENCE: 5

```
atcgaattaa agtca atg gcg tca cgt tta tgt ctt ctc ctt ctc gtt gcg      51
            Met Ala Ser Arg Leu Cys Leu Leu Leu Leu Val Ala
              1               5                  10 tgt atc gcc gga gca ttt gcc gga gac gtc atc gaa ctc aat cga tct      99
Cys Ile Ala Gly Ala Phe Ala Gly Asp Val Ile Glu Leu Asn Arg Ser
         15              20                  25 cag agg gag ttc gat tat ttc gct cta tct ctt caa tgg cct gga acc     147
Gln Arg Glu Phe Asp Tyr Phe Ala Leu Ser Leu Gln Trp Pro Gly Thr
 30              35                  40 tat tgc cgt gga act cgc cat tgt tgc tcc aaa aac gct tgc tgc aga     195
Tyr Cys Arg Gly Thr Arg His Cys Cys Ser Lys Asn Ala Cys Cys Arg
 45              50                  55                      60 ggc tcc gat gct cca act caa ttc aca att cat ggg tta tgg cct gac     243
Gly Ser Asp Ala Pro Thr Gln Phe Thr Ile His Gly Leu Trp Pro Asp
                 65                  70                  75 tat aac gat ggt tcg tgg cct tca tgt tgt tat cga tct gac ttt aaa     291
Tyr Asn Asp Gly Ser Trp Pro Ser Cys Cys Tyr Arg Ser Asp Phe Lys
             80                  85                  90 gag aag gag att tca acg ttg atg gat ggt ctt gag aag tac tgg cct     339
Glu Lys Glu Ile Ser Thr Leu Met Asp Gly Leu Glu Lys Tyr Trp Pro
         95                  100                 105 agt ctc agt tgt ggt tct cca tca tca tgc aat ggt ggg aaa ggg tca     387
Ser Leu Ser Cys Gly Ser Pro Ser Ser Cys Asn Gly Gly Lys Gly Ser
110                 115                 120 ttt tgg ggc cac gag tgg gag aaa cat ggg act tgt tct tct cct gtt     435
Phe Trp Gly His Glu Trp Glu Lys His Gly Thr Cys Ser Ser Pro Val
125                 130                 135                 140 ttt cat gat gag tat aat tac ttc ctt acc aca ctt aat ctc tac ttg     483
Phe His Asp Glu Tyr Asn Tyr Phe Leu Thr Thr Leu Asn Leu Tyr Leu
                145                 150                 155 aag cat aat gtc acg gat gtc ctt tat caa gct ggc tat gtt gct tcc     531
Lys His Asn Val Thr Asp Val Leu Tyr Gln Ala Gly Tyr Val Ala Ser
            160                 165                 170 aac agt gaa aag tat cct cta gga ggt atc gta aca gcc att cag aat     579
Asn Ser Glu Lys Tyr Pro Leu Gly Gly Ile Val Thr Ala Ile Gln Asn
        175                 180                 185 gca ttt cat atc acc cct gaa gtg gtt tgc aaa aga gat gca atc gat     627
Ala Phe His Ile Thr Pro Glu Val Val Cys Lys Arg Asp Ala Ile Asp
    190                 195                 200 gaa ata cgt ata tgc ttc tat aaa gat ttt aag ccc agg gac tgt gtt     675
Glu Ile Arg Ile Cys Phe Tyr Lys Asp Phe Lys Pro Arg Asp Cys Val
205                 210                 215                 220 ggt tca caa gat ttg aca tct aga aag tca tgc ccc aag tac gta agt     723
Gly Ser Gln Asp Leu Thr Ser Arg Lys Ser Cys Pro Lys Tyr Val Ser
                225                 230                 235 ttg ccg gaa tac acg cca tta gat ggt gaa gct atg gtt ctg aag atg     771
Leu Pro Glu Tyr Thr Pro Leu Asp Gly Glu Ala Met Val Leu Lys Met
            240                 245                 250
```

```
cca aca gaa aga gaa gct ctt tga atcggaaaag atgggagctt tgttatcttc      825
Pro Thr Glu Arg Glu Ala Leu
        255 tgagagacaa tacatacatg tctctgatgt tgtaacttta ctaccaaaac ctataaagat      885 tggcttattt cgttctattg gatatgtatc atcattactg gtaaatcaag tttcttctta      945 ataatgtaga agatcagaaa atccataaga agatatcaac atttgagttc tatggtaaaa     1005 aaaaaaa                                                                1012
```

<210> SEQ ID NO 6
<211> LENGTH: 259
<212> TYPE: PRT
<213> ORGANISM: Arabidopsis thaliana

<400> SEQUENCE: 6

```
Met Ala Ser Arg Leu Cys Leu Leu Leu Val Ala Cys Ile Ala Gly
 1               5                  10                  15

Ala Phe Ala Gly Asp Val Ile Glu Leu Asn Arg Ser Gln Arg Glu Phe
                20                  25                  30

Asp Tyr Phe Ala Leu Ser Leu Gln Trp Pro Gly Thr Tyr Cys Arg Gly
            35                  40                  45

Thr Arg His Cys Cys Ser Lys Asn Ala Cys Cys Arg Gly Ser Asp Ala
        50                  55                  60

Pro Thr Gln Phe Thr Ile His Gly Leu Trp Pro Asp Tyr Asn Asp Gly
 65                  70                  75                  80

Ser Trp Pro Ser Cys Cys Tyr Arg Ser Asp Phe Lys Glu Lys Glu Ile
                85                  90                  95

Ser Thr Leu Met Asp Gly Leu Glu Lys Tyr Trp Pro Ser Leu Ser Cys
           100                 105                 110

Gly Ser Pro Ser Ser Cys Asn Gly Gly Lys Gly Ser Phe Trp Gly His
       115                 120                 125

Glu Trp Glu Lys His Gly Thr Cys Ser Ser Pro Val Phe His Asp Glu
   130                 135                 140

Tyr Asn Tyr Phe Leu Thr Thr Leu Asn Leu Tyr Leu Lys His Asn Val
145                 150                 155                 160

Thr Asp Val Leu Tyr Gln Ala Gly Tyr Val Ala Ser Asn Ser Glu Lys
                165                 170                 175

Tyr Pro Leu Gly Gly Ile Val Thr Ala Ile Gln Asn Ala Phe His Ile
            180                 185                 190

Thr Pro Glu Val Val Cys Lys Arg Asp Ala Ile Asp Glu Ile Arg Ile
        195                 200                 205

Cys Phe Tyr Lys Asp Phe Lys Pro Arg Asp Cys Val Gly Ser Gln Asp
    210                 215                 220

Leu Thr Ser Arg Lys Ser Cys Pro Lys Tyr Val Ser Leu Pro Glu Tyr
225                 230                 235                 240

Thr Pro Leu Asp Gly Glu Ala Met Val Leu Lys Met Pro Thr Glu Arg
                245                 250                 255

Glu Ala Leu
```

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Made in lab
<220> FEATURE:
<221> NAME/KEY: modified_base

```
<222> LOCATION: (3)
<223> OTHER INFORMATION: n=i
<220> FEATURE:
<221> NAME/KEY: modified_base
<222> LOCATION: (6)
<223> OTHER INFORMATION: n=i
<220> FEATURE:
<221> NAME/KEY: modified_base
<222> LOCATION: (9)
<223> OTHER INFORMATION: n=i
<220> FEATURE:
<221> NAME/KEY: modified_base
<222> LOCATION: (12)
<223> OTHER INFORMATION: n=i
<220> FEATURE:
<221> NAME/KEY: modified_base
<222> LOCATION: (15)
<223> OTHER INFORMATION: n=i

<400> SEQUENCE: 7
gcngtnagny cntcncccat                                               20

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence:Made in lab
<220> FEATURE:
<221> NAME/KEY: modified_base
<222> LOCATION: (6)
<223> OTHER INFORMATION: n=i
<220> FEATURE:
<221> NAME/KEY: modified_base
<222> LOCATION: (12)
<223> OTHER INFORMATION: n=i
<220> FEATURE:
<221> NAME/KEY: modified_base
<222> LOCATION: (15)
<223> OTHER INFORMATION: n=i

<400> SEQUENCE: 8
aaycgncarg tnacntt                                                  17

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence:Made in lab

<400> SEQUENCE: 9
cgccttcttc aataaaccat ttcggcgctt                                    30

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence:Made in lab

<400> SEQUENCE: 10
gacctgtcgg ttcgtagtat tttcaatcct                                    30

<210> SEQ ID NO 11
<211> LENGTH: 30
<212> TYPE: DNA
<213> ORGANISM: Artificial Sequence
<220> FEATURE:
<223> OTHER INFORMATION: Description of Artificial Sequence:Made in lab
```

```
<400> SEQUENCE: 11
ttcgtcctcc attttgtgcg ctctccattc                                        30

<210> SEQ ID NO 12
<211> LENGTH: 30
<212> TYPE: DNA
<213> ORGANISM: Artificial Sequence
<220> FEATURE:
<223> OTHER INFORMATION: Description of Artificial Sequence:Made in lab

<400> SEQUENCE: 12
gcactccact cttcctttat ttcttaccac                                        30

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence:Made in lab

<400> SEQUENCE: 13
agttacttaa caatgcgcaa ccaaggc                                           27

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence:Made in lab

<400> SEQUENCE: 14
ttgtgtacaa atcatggg                                                     18

<210> SEQ ID NO 15
<211> LENGTH: 18
<212> TYPE: DNA
<213> ORGANISM: Artificial Sequence
<220> FEATURE:
<223> OTHER INFORMATION: Description of Artificial Sequence:Made in lab

<400> SEQUENCE: 15
gtaagcccgt cacccatc                                                     18

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence:Made in lab

<400> SEQUENCE: 16
gaacaagatg gattgcacgc                                                   20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence:Made in lab

<400> SEQUENCE: 17
gaagaactcg tcaagaaggc                                                   20
```